US008974477B2

(12) United States Patent
Yamada

(10) Patent No.: US 8,974,477 B2
(45) Date of Patent: Mar. 10, 2015

(54) ULTRASONIC OPERATING APPARATUS

(75) Inventor: Norihiro Yamada, Hino (JP)

(73) Assignee: Olympus Medical Systems Corp. (JP)

( * ) Notice: Subject to any disclaimer, the term of this patent is extended or adjusted under 35 U.S.C. 154(b) by 1379 days.

(21) Appl. No.: 12/201,005

(22) Filed: Aug. 29, 2008

(65) Prior Publication Data

US 2010/0057117 A1  Mar. 4, 2010

(51) Int. Cl.
*A61B 17/32* (2006.01)

(52) U.S. Cl.
CPC .............................. *A61B 17/320092* (2013.01)
USPC ........................................................ 606/169

(58) Field of Classification Search
USPC ............... 606/169, 170, 171, 205, 40, 50, 51, 606/206–210; 604/22; 600/104, 106, 437, 600/562–570, 167; 601/2
See application file for complete search history.

(56) References Cited

U.S. PATENT DOCUMENTS

| 4,646,738 | A | * | 3/1987 | Trott | 606/170 |
| 5,478,351 | A | * | 12/1995 | Meade et al. | 606/205 |
| 5,922,003 | A | * | 7/1999 | Anctil et al. | 606/170 |
| 5,980,510 | A | * | 11/1999 | Tsonton et al. | 606/1 |
| 6,036,636 | A | * | 3/2000 | Motoki et al. | 600/146 |
| 2002/0077643 | A1 | * | 6/2002 | Rabiner et al. | 606/169 |
| 2002/0165564 | A1 | * | 11/2002 | Danitz et al. | 606/151 |
| 2003/0195419 | A1 | * | 10/2003 | Harada | 600/437 |
| 2005/0049525 | A1 | * | 3/2005 | Yamada et al. | 601/2 |
| 2006/0058825 | A1 | * | 3/2006 | Ogura et al. | 606/169 |
| 2006/0259054 | A1 | * | 11/2006 | Masuda et al. | 606/169 |
| 2007/0043352 | A1 | * | 2/2007 | Garrison et al. | 606/51 |

* cited by examiner

*Primary Examiner* — Jocelin Tanner
(74) *Attorney, Agent, or Firm* — Ostrolenk Faber LLP

(57) ABSTRACT

In an ultrasonic operating apparatus which is provided with an insertion portion including a sheath having a distal end and a proximal end and formed of a cylindrical body having at least partially flexibility and a procedure portion disposed at the distal end of the sheath and performing a procedure for resection of a body tissue, and an operation portion disposed at the proximal end of the sheath and operating the procedure portion, the procedure portion is provided with an ultrasonic transducer unit including an ultrasonic transducer generating ultrasonic vibration, a probe portion integrally coupled with the ultrasonic transducer and transmitted with ultrasonic waves output from the ultrasonic transducer, and a casing accommodating the ultrasonic transducer, a jaw caused to face the probe portion which configures a distal end of the ultrasonic transducer and including a supporting point held in a state that the supporting point is not moved to the probe portion axially relative to the probe portion and an operating point movable axially relative to the probe portion, the jaw being driven to be opened and closed to the probe portion, a cover member coupled to the distal end of the sheath and rotatably supporting the operating point of the jaw, and a supporting portion disposed at a distal end of the casing and supporting the supporting point of the jaw, the operation portion is provided with a movable handle moving the operating point of the jaw axially relative to the probe member via the sheath and the cover member and rotating the jaw about the supporting point to drive the jaw to be opened and closed to the probe portion, and the jaw is set in a state that the operating point and the supporting point are positioned on a line orthogonal to a center line of the probe portion in a state that the jaw has been closed to the probe portion.

14 Claims, 15 Drawing Sheets

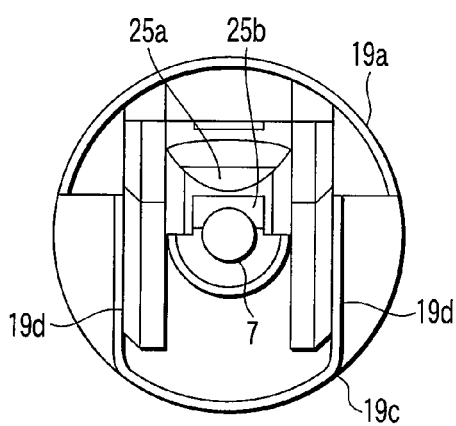
F I G. 5
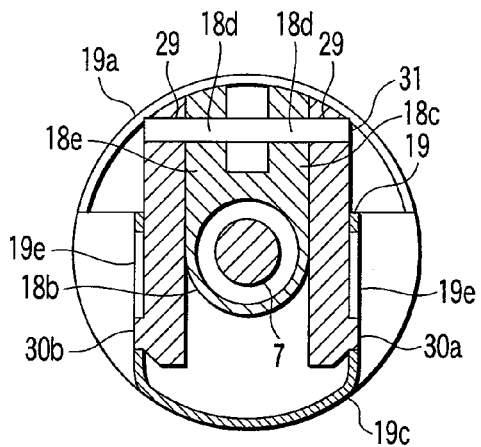
F I G. 6
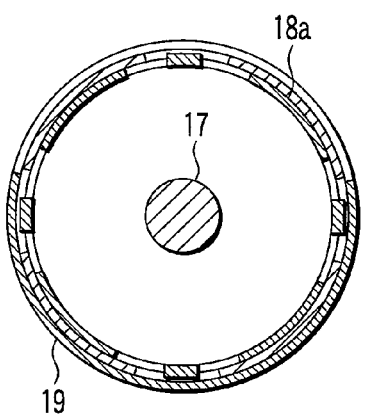
F I G. 7
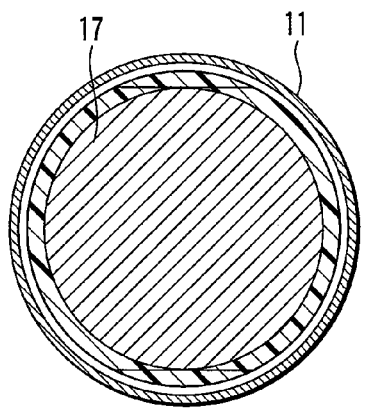
F I G. 8
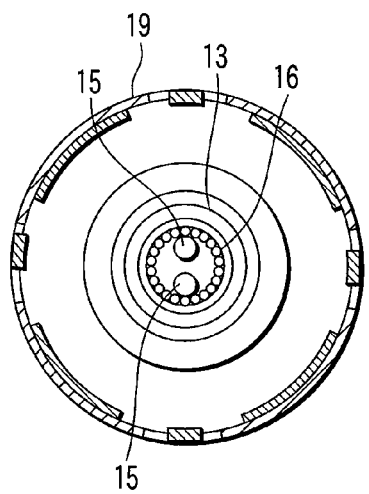
F I G. 9

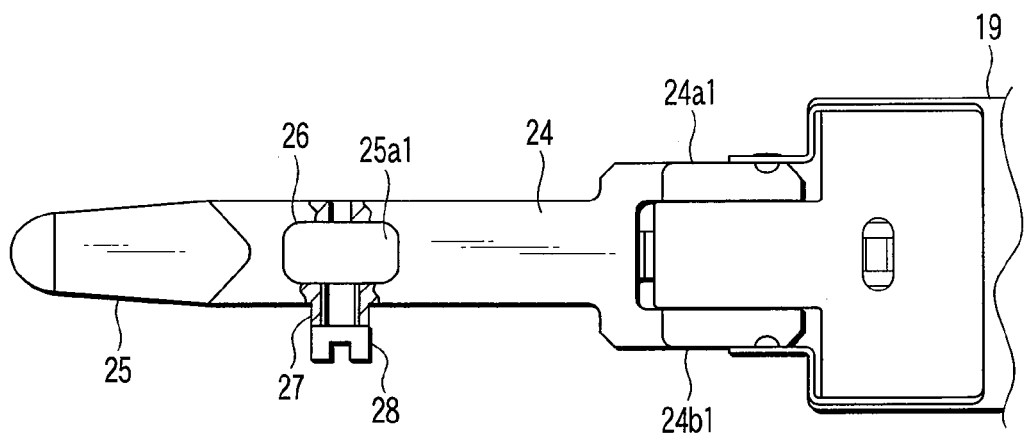
F I G. 13
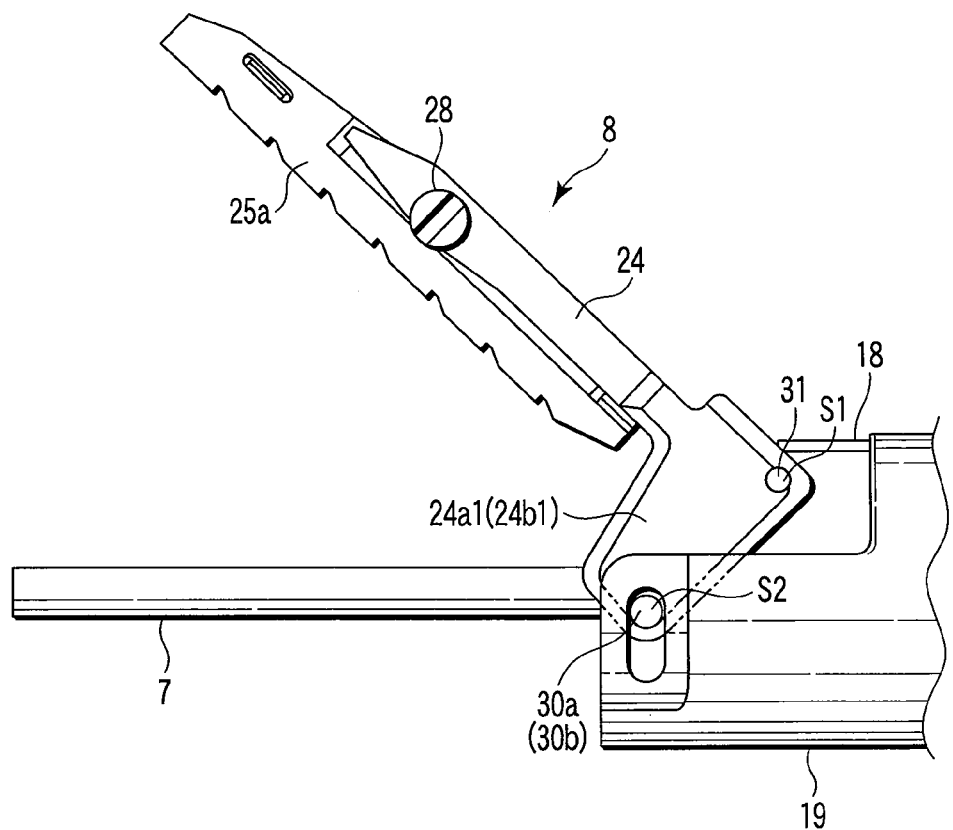
F I G. 14

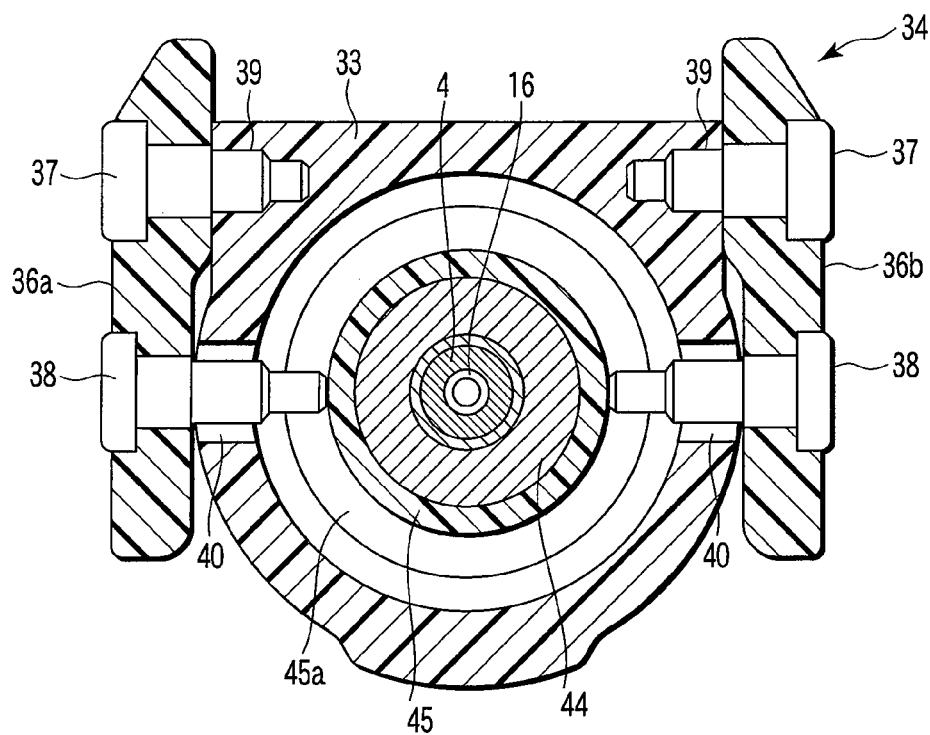
F I G. 17
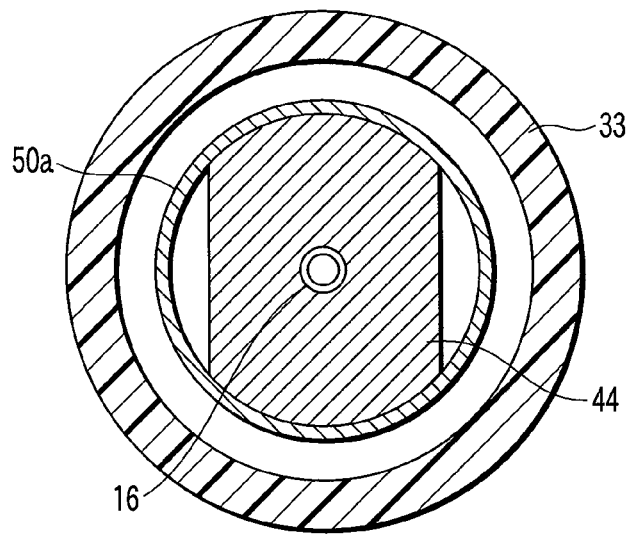
F I G. 18

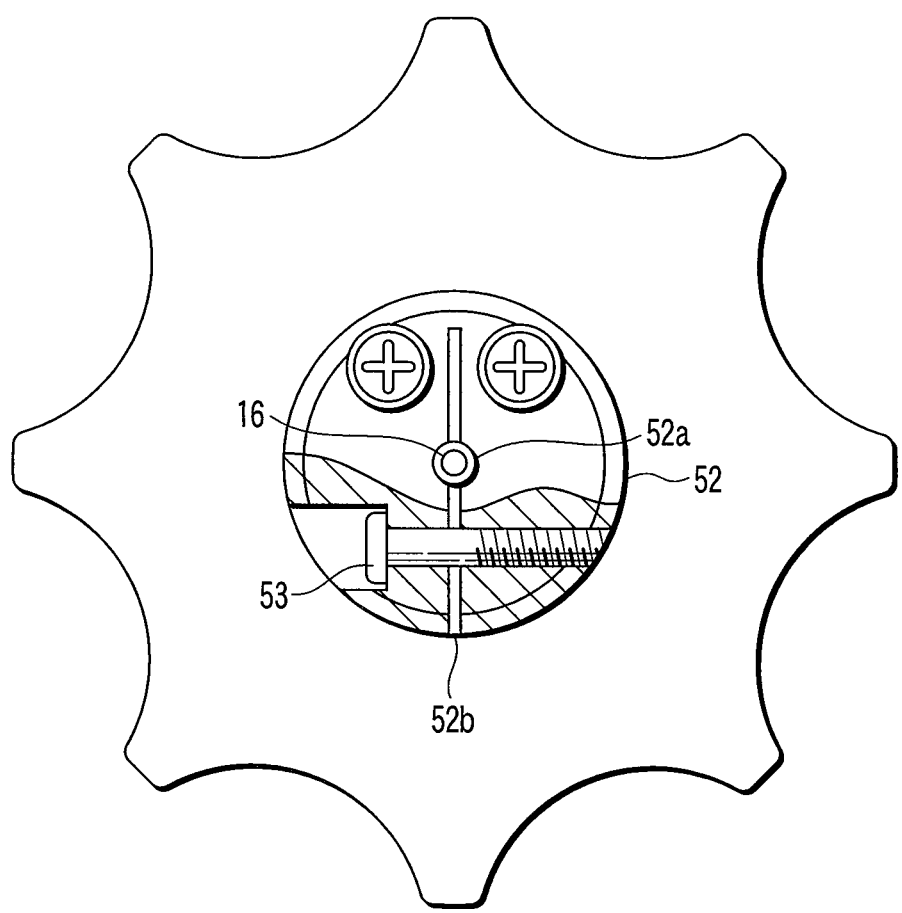
F I G. 19

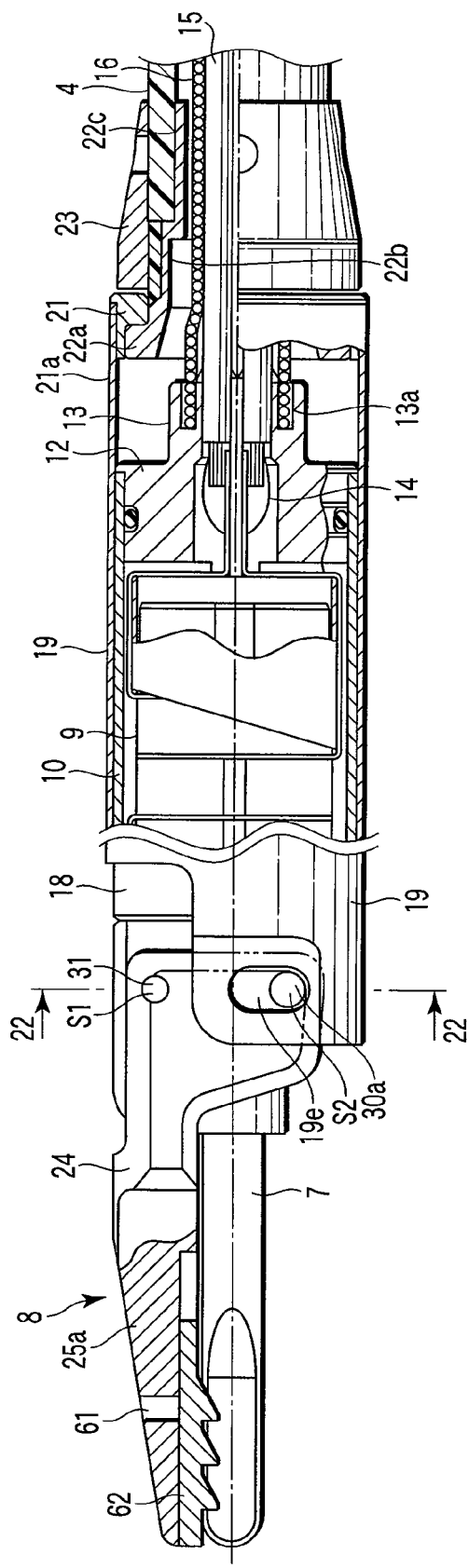
FIG. 20
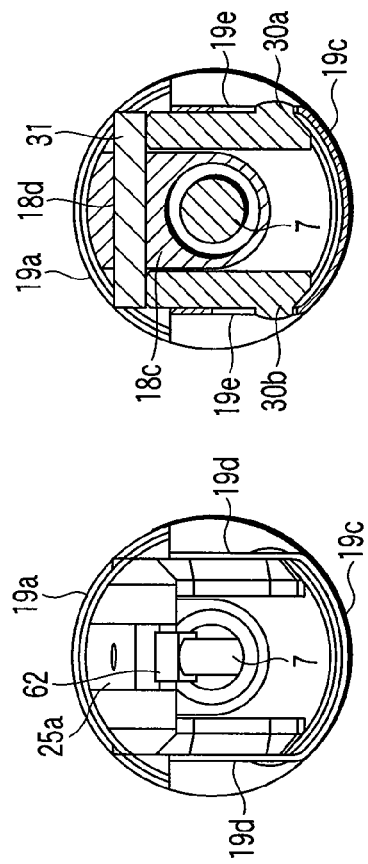
FIG. 21
FIG. 22

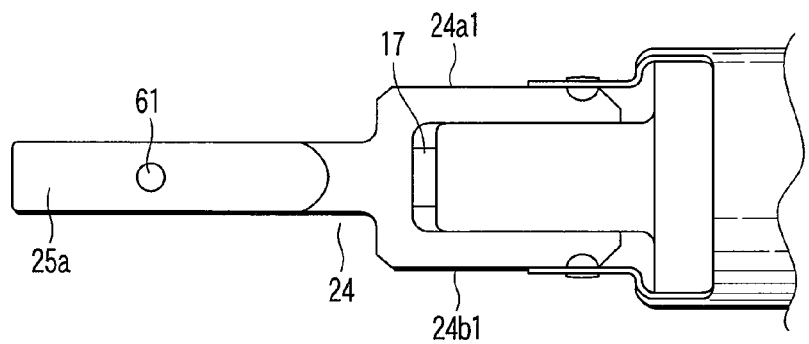
F I G. 23
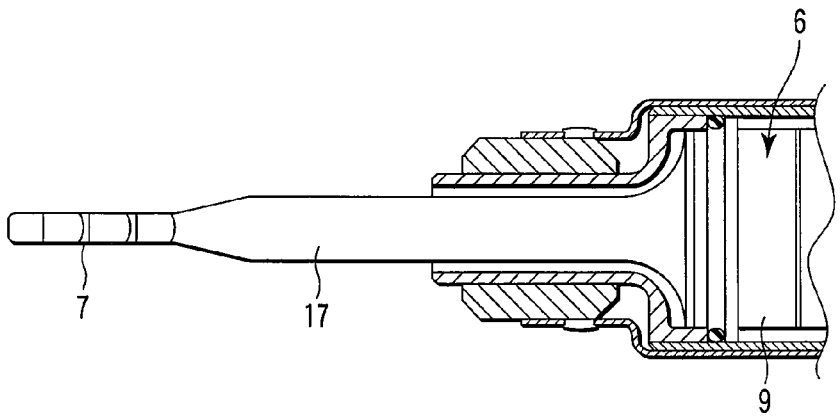
F I G. 24
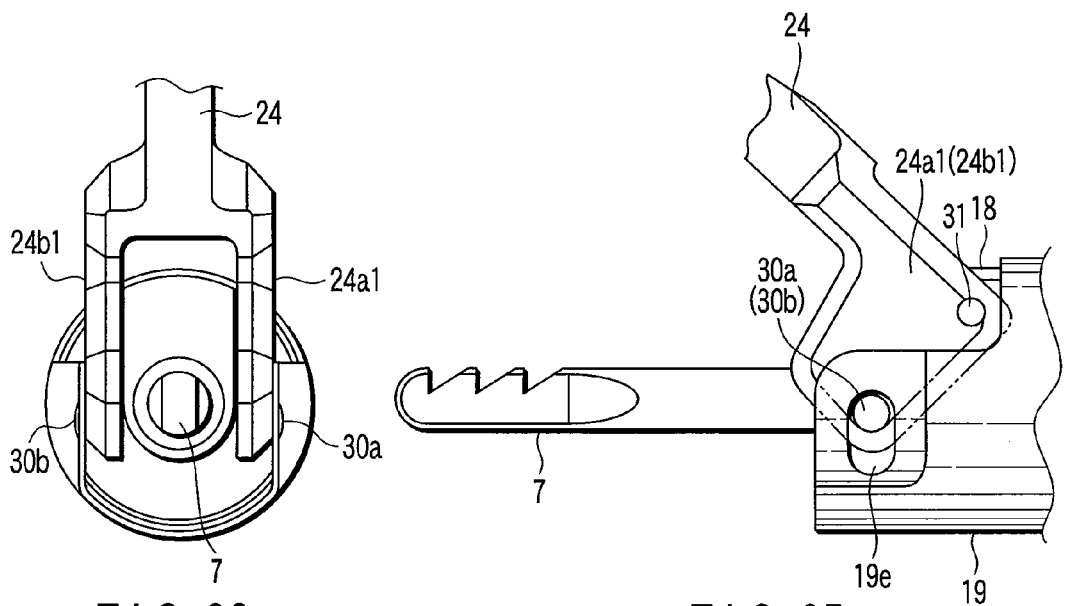
F I G. 26
F I G. 25

ULTRASONIC OPERATING APPARATUS

BACKGROUND OF THE INVENTION

The present invention relates to an ultrasonic operating apparatus which performs a procedure such as incising, resection, or clotting of a body tissue utilizing ultrasonic waves.

As one example of an ordinary ultrasonic operating apparatus which performs a procedure such as incising, resection, or clotting of a body tissue utilizing ultrasonic waves, there is an ultrasonic clotting and incising apparatus disclosed in U.S. Pat. No. 5,980,510 (Patent Document 1), for example. In the apparatus, an operation portion on a near side is coupled to a proximal end of an elongated insertion portion. An ultrasonic transducer generating ultrasonic vibration is disposed in the operation portion. A procedure portion for treating a body tissue is disposed at a distal end of the insertion portion.

The insertion portion includes an elongated circular tubular sheath. A rod-like vibration transmission member (probe) is inserted into the sheath. A proximal end of the vibration transmission member is connected to an ultrasonic transducer via a connection portion of a screwing type in an attachable and detachable manner. Ultrasonic vibration generated by the ultrasonic transducer is transmitted to a cylindrical probe distal end at a distal end side of the vibration transmission member.

A clamp arm is disposed on the procedure portion to face the probe distal end. A pad with asperity is fixed to the clamp arm. Here, an arm holding member holding the clamp arm is provided at a distal end of the sheath of the insertion portion. A proximal end of the clamp arm is rotatably supported by an arm holding member holding the clamp arm via a supporting shaft. An operation member driving the clamp arm is inserted in the sheath so as to be capable of advancing and retreating axially relative to the sheath. An operation handle is disposed on the operation portion. The operation member is driven so as to advance and retreat axially according to operation of the operation handle. The clamp arm is operated to be opened and closed to the probe distal end in association with action of the operation member.

A body tissue is grasped between the cylindrical probe distal end and the pad of the clamp arm at a closing operation time of the clamp arm. In this state, ultrasonic vibration from the ultrasonic transducer is transmitted to the probe distal end on the procedure portion side via the vibration transmission member, so that a procedure such as incising, resection, or clotting of a body tissue is performed utilizing ultrasonic waves.

BRIEF SUMMARY OF THE INVENTION

According to an aspect of the present invention, there is provided an ultrasonic operating apparatus which is provided with an insertion portion including a sheath having a distal end and a proximal end and formed of a cylindrical body having at least partially flexibility and a procedure portion disposed at the distal end of the sheath and performing a procedure for resection of a body tissue, and an operation portion disposed at the proximal end of the sheath and operating the procedure portion, wherein the procedure portion comprises an ultrasonic transducer unit including an ultrasonic transducer generating ultrasonic vibration, a probe portion integrally coupled with the ultrasonic transducer and transmitted with ultrasonic waves output from the ultrasonic transducer, and a casing accommodating the ultrasonic transducer; a jaw caused to face the probe portion which configures a distal end of the ultrasonic transducer and including a supporting point held in a state that the supporting point is not moved to the probe portion axially thereto and an operating point movable axially relative to the probe portion, the jaw being driven to be opened and closed to the probe portion; a cover member coupled to the distal end of the sheath and rotatably supporting the operating point of the jaw; and a supporting portion disposed at a distal end of the casing and supporting the supporting point of the jaw, the operation portion comprises a movable handle moving the operating point of the jaw axially relative to the probe portion via the sheath and the cover member and rotating the jaw about the supporting point to drive the jaw to be opened and closed to the probe portion, and the jaw is set in a state that the operating point and the supporting point are positioned on a line orthogonal to a center line of the probe portion in a state that the jaw has been closed to the probe portion.

It is preferable that the cover member is coupled to the distal end of the sheath rotatably realative to the probe portion in a state that axial movement of the probe portion follows the sheath.

It is preferable that the sheath is a flexible pipe where a blade which is a mesh pipe made of metal wire is received in a resin tube.

It is preferable that the operating portion includes a slider movable axially relative to the sheath, a guide member guiding movement of the slider, a supporting portion rotatably supporting the movable handle, and an actuating portion moving the slider axially relative to the sheath in association with rotating action of the movable handle about the supporting member, and the sheath includes a fixation portion fixed with the slider at the proximal end thereof and moves axially relative to the sheath in association with opening and closing actions of the movable handle.

It is preferable that the operation portion includes a rotatable knob rotating circumferentially relative to the sheath, the sheath includes a coil shaft with a distal end and a proximal end in the sheath, and the proximal end of the coil shaft is connected to the rotatable knob and the distal end of the coil shaft is fixed to the casing.

It is preferable that the sheath includes a hard pipe body formed of a hard tubular body and having a distal end and a proximal end, and a bending portion coupled to the distal end of the hard pipe body and deformable in a bending manner.

It is preferable that the ultrasonic transducer is set to have the entire length of a half wavelength and is fixed to the casing at a position of a node portion of vibrations near the middle of the ultrasonic transducer.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a front view showing the distal end of the procedure portion shown in FIG. 3 as viewed from the front thereof;

FIG. 6 is a VI-VI sectional view of FIG. 3;

FIG. 7 is a VII-VII sectional view of FIG. 3;

FIG. 8 is a VIII-VIII sectional view of FIG. 4;

FIG. 9 is a IX-IX sectional view of FIG. 4;

FIG. 13 is a plan view showing a surrounding portion of the jaw of the ultrasonic clotting and incising apparatus according to the first embodiment;

FIG. 14 is a side view showing a state that the jaw of the ultrasonic clotting and incising apparatus according to the first embodiment has been operated for opening;

FIG. 17 is a 17-17 sectional view of FIG. 16;

FIG. 18 is a 18-18 sectional view of FIG. 16;

FIG. 19 is a side view showing a coil shaft fixing member of a rotatable knob of the operation portion of the ultrasonic clotting and incising apparatus according to the first embodiment in a partially sectioned manner;

FIG. 20 is a side view of a procedure portion of an ultrasonic clotting and incising apparatus according to a second embodiment of the present invention in a partially sectioned manner;

FIG. 21 is a 21-21 sectional view of FIG. 20;

FIG. 22 is a 22-22 sectional view of FIG. 20;

FIG. 23 is a plan view showing an attaching state of a jaw of the procedure portion of the ultrasonic clotting and incising apparatus according to the second embodiment;

FIG. 24 is a vertical sectional view showing an attaching state of an ultrasonic transducer unit of the procedure portion of the ultrasonic clotting and incising apparatus according to the second embodiment;

FIG. 25 is a side view showing a state that the jaw of the ultrasonic clotting and incising apparatus according to the second embodiment has been operated for opening;

FIG. 26 is a front view of a probe portion in a state that the jaw has been operated for opening, as viewed from a front face side of the probe portion.

DETAILED DESCRIPTION OF THE INVENTION

Figure 1:
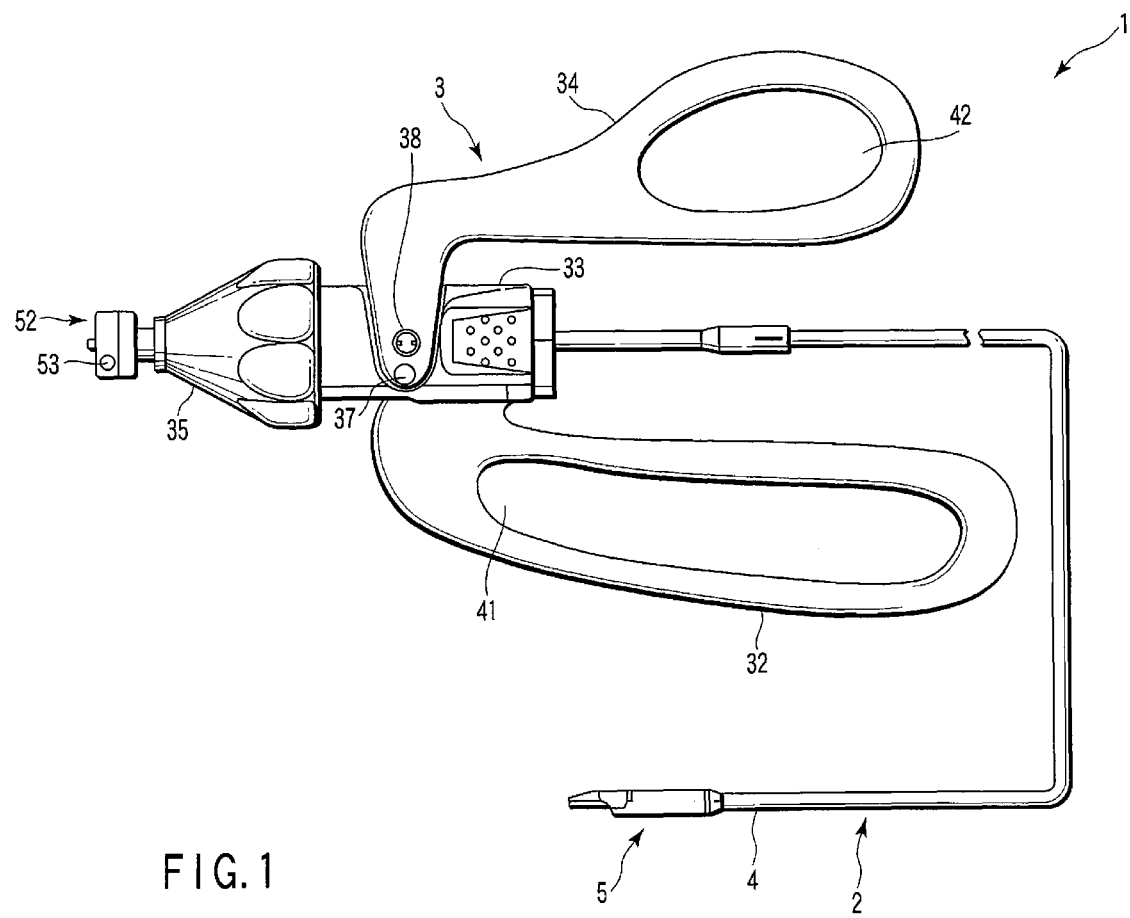
FIG. 1 is a side view showing a whole schematic configuration of an ultrasonic clotting and incising apparatus according to a first embodiment of the present invention.

A first embodiment of the present invention will be explained below with reference to FIG. 1 to FIG. 19. FIG. 1 shows a whole schematic configuration of an ultrasonic clotting and incising apparatus 1 which is an ultrasonic operating apparatus according to the first embodiment. The ultrasonic clotting and incising apparatus 1 is provided with an elongated insertion portion 2 inserted in a body and an operation portion 3 coupled to a proximal end of the insertion portion 2. The insertion portion 2 is provided with a sheath 4 having a distal end and a proximal end and formed of a flexible cylindrical body, and a distal end unit 5 disposed at a distal end of the sheath 4. The sheath 4 is a flexible pipe where a blade which is a mesh pipe made of metal wire (for example, stainless wire) is received in a resin tube.

Figure 2:
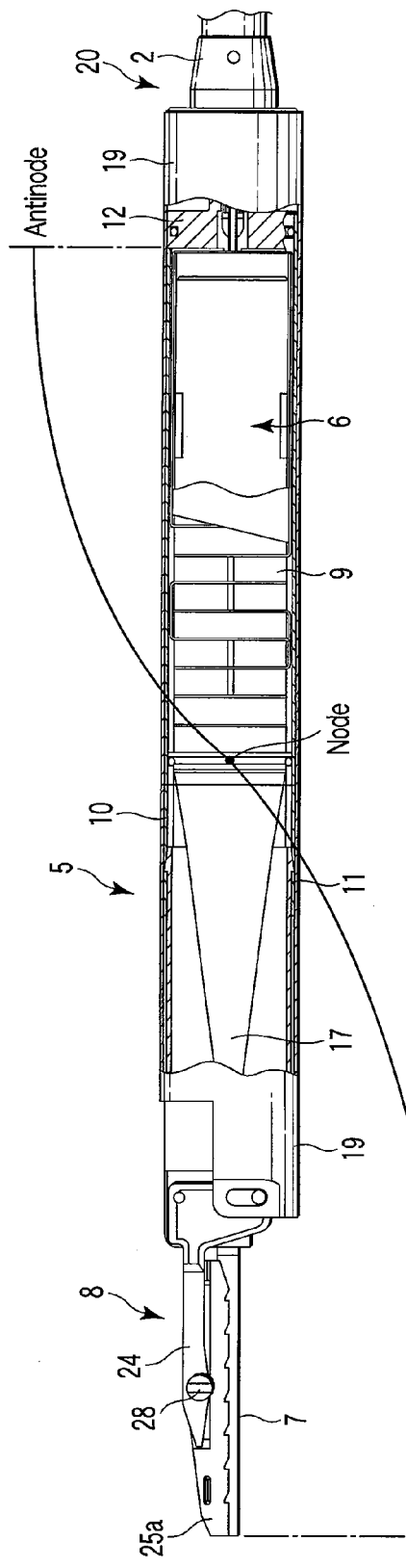
FIG. 2 is a side view showing a procedure portion of the ultrasonic clotting and incising apparatus according to the first embodiment in a partially sectioned manner.

FIG. 2 is a side view showing of the distal end unit 5 of the ultrasonic clotting and incising apparatus 1 in a partially sectioned manner. The distal end unit 5 is mainly provided with an ultrasonic transducer unit 6, a probe portion 7, and a jaw 8. A distal end procedure potion which performs treatment for resection of a body tissue is configured by the probe portion 7 and the jaw 8.

Figure 4:
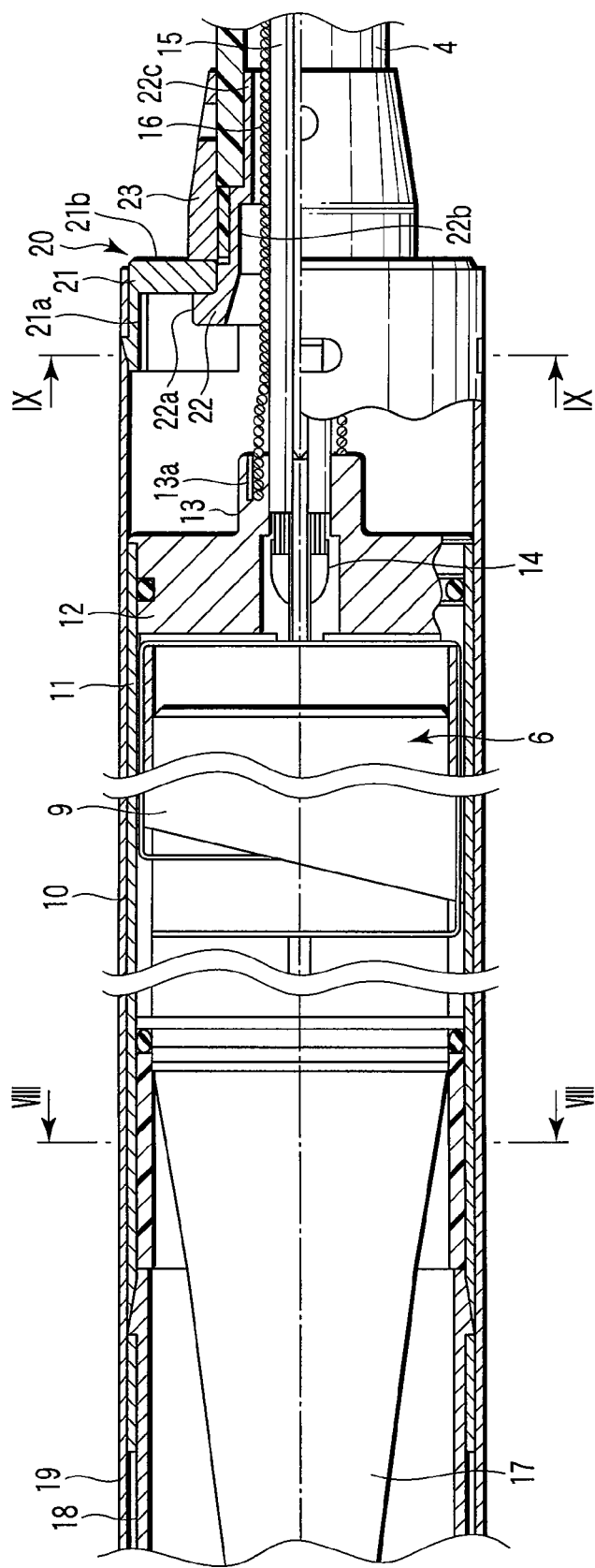
FIG. 4 is a vertical sectional view showing a rear end of the procedure portion of the ultrasonic clotting and incising apparatus according to the first embodiment in an enlarged manner.

As shown in FIG. 4, the ultrasonic transducer unit 6 includes an ultrasonic transducer 9 generating ultrasonic vibration and a casing 10 accommodating the ultrasonic transducer 9 therein. The ultrasonic transducer 9 is a bolted Langevin transducer. The casing 10 includes a cylindrical cylinder 11. An end plate 12 is provided at a proximal end of the casing 10. The end plate 12 closes a rear end opening portion of the cylindrical cylinder 11.

A boss portion 13 is provided on a central portion of a back of the end plate 12 so as to project rearward. A circular hole 13a is formed at a central portion of the boss portion 13. A wire connection portion 14 for the ultrasonic transducer 9 is provided at a central portion of the end plate 12. Distal ends of two wire cords 15 are connected to the wire connection portion 14, respectively. Proximal ends of the two wire cords 15 are connected to an ultrasonic power source apparatus (not shown). The ultrasonic transducer 9 is driven by supplying power from the ultrasonic power source apparatus to the ultrasonic transducer 9 via two wire cords 15.

The two wire cords 15 are inserted in a coil shaft 16 transmitting rotating force about circumferentially (described later). A distal end of the coil shaft 16 is fixed on an inner peripheral surface of the hole 13a of the boss portion 13 using such means as adhesion in a state that it has been inserted in the hole 13a of the boss portion 13.

A distal end of the ultrasonic transducer 9 is integrally coupled to a proximal end of a rod-shaped probe portion 7 via an approximately conical horn 17. Ultrasonic vibration generated at the ultrasonic transducer 9 is amplified via the horn 17 to be transmitted to the probe portion 7.

A horn cover 18 is fixed at the distal end of the cylinder 11 at a distal end of the casing 10. As shown in FIGS. 12A to 12D, the horn cover 18 includes a small-diameter portion 18*b* formed at the distal end of a cylindrical horn cover main body 18*a*. The small-diameter portion 18*b* is formed with an extended portion 18*c* extending upwardly in FIGS. 12C and 12D. The extended portion 18*c* is formed with a pin insertion hole 18*d*. The pin insertion hole 18*d* is formed to be parallel with a line orthogonal to the center line of a horn cover main body 18*a*.

A cover member 19 is disposed on an outer peripheral surface of the casing 10. The cover member 19 is assembled so as to movable relative to the casing 10 in a direction of the center line of the casing 10.

Figure 11A:
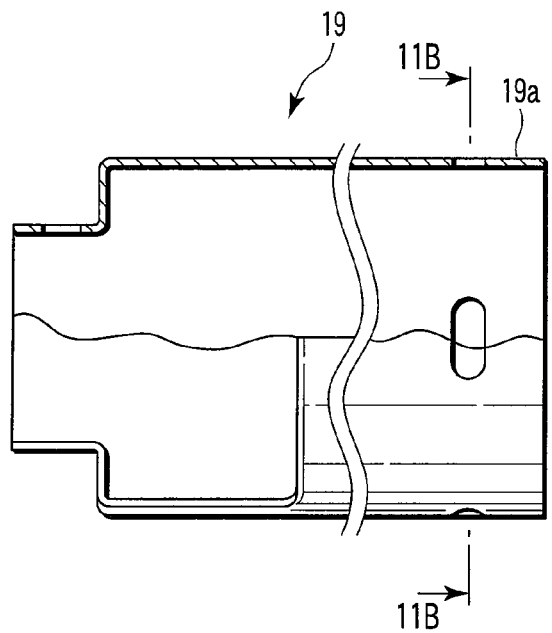
FIG. 11A is a side view showing a cover member of the ultrasonic clotting and incising apparatus according to the first embodiment in a partially sectioned manner.
Figure 11B:
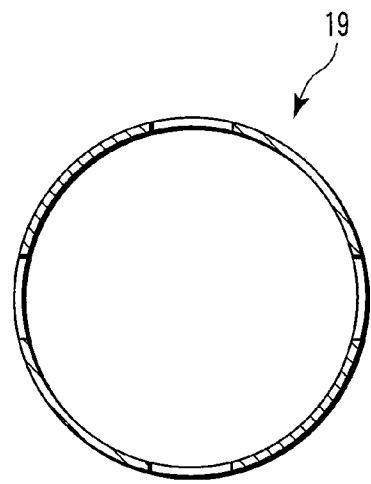
FIG. 11B is a 11B-11B sectional view of FIG. 11A.
Figures 11C, 11D:
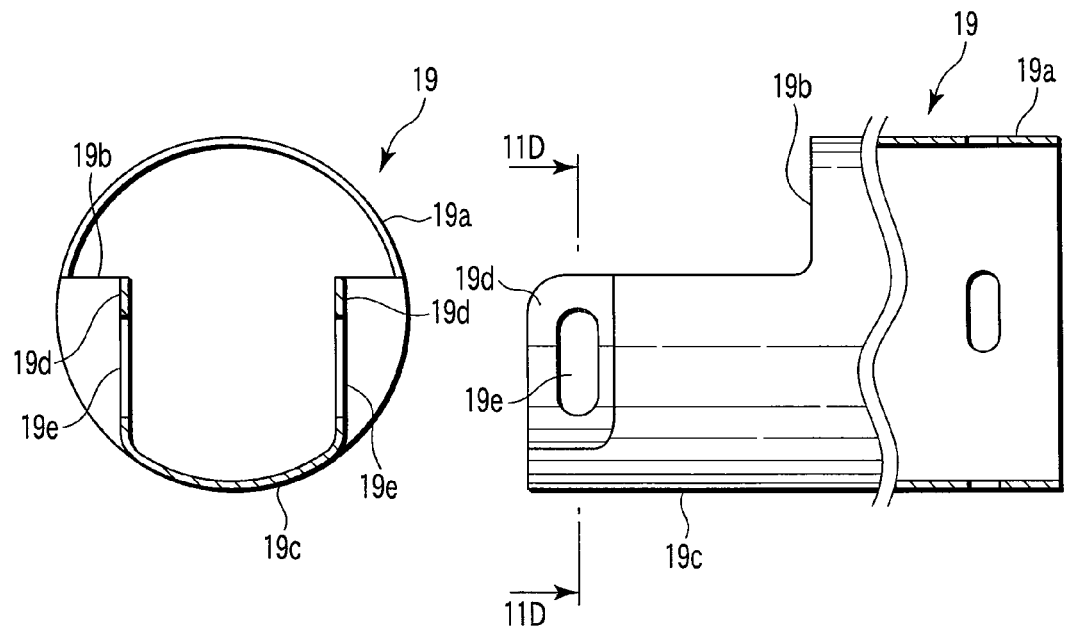
FIG. 11C is a side view showing the cover member of the ultrasonic clotting and incising apparatus according to the first embodiment in a partially sectioned manner.
FIG. 11D is a 11D-11D sectional view of FIG. 11C.
Figure 12A:
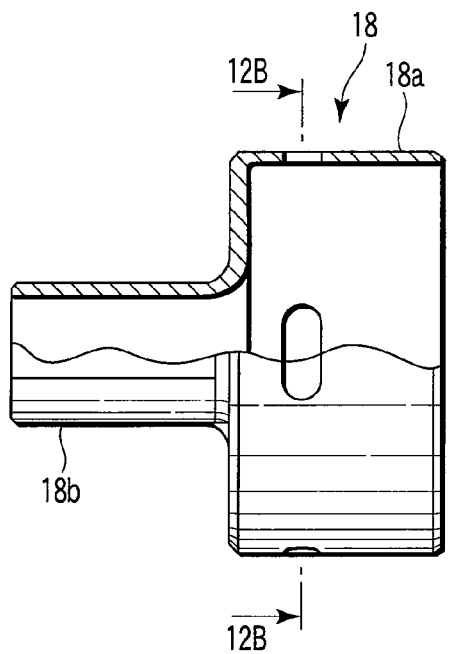
FIG. 12A is a side view of a horn cover of the ultrasonic clotting and incising apparatus according to the first embodiment in a partially sectioned manner.
Figure 12B:
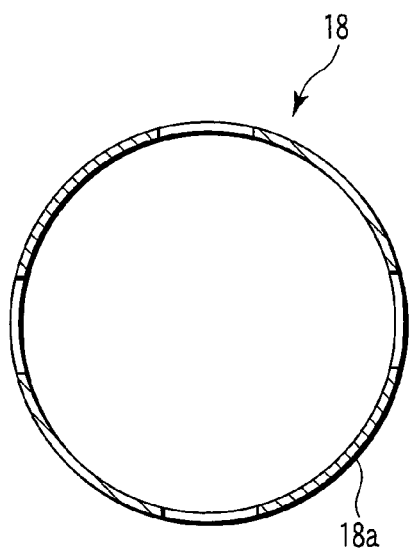
FIG. 12B is a 12B-12B sectional view of FIG. 12A.
Figure 12D:
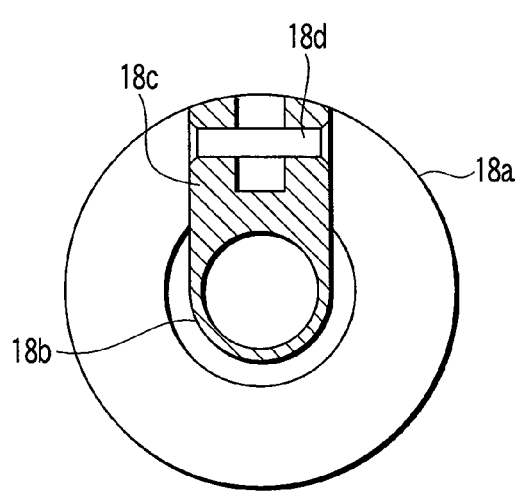
FIG. 12D is a 12D-12D sectional view of FIG. 12C.
Figure 12C:
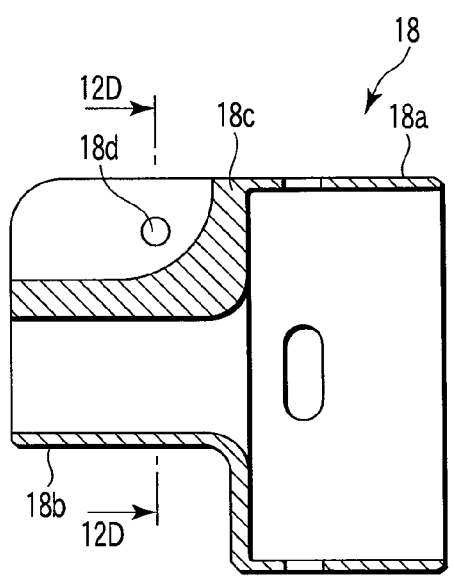
FIG. 12C is a vertical sectional view of the horn cover of the ultrasonic clotting and incising apparatus according to the first embodiment.
Figure 15:
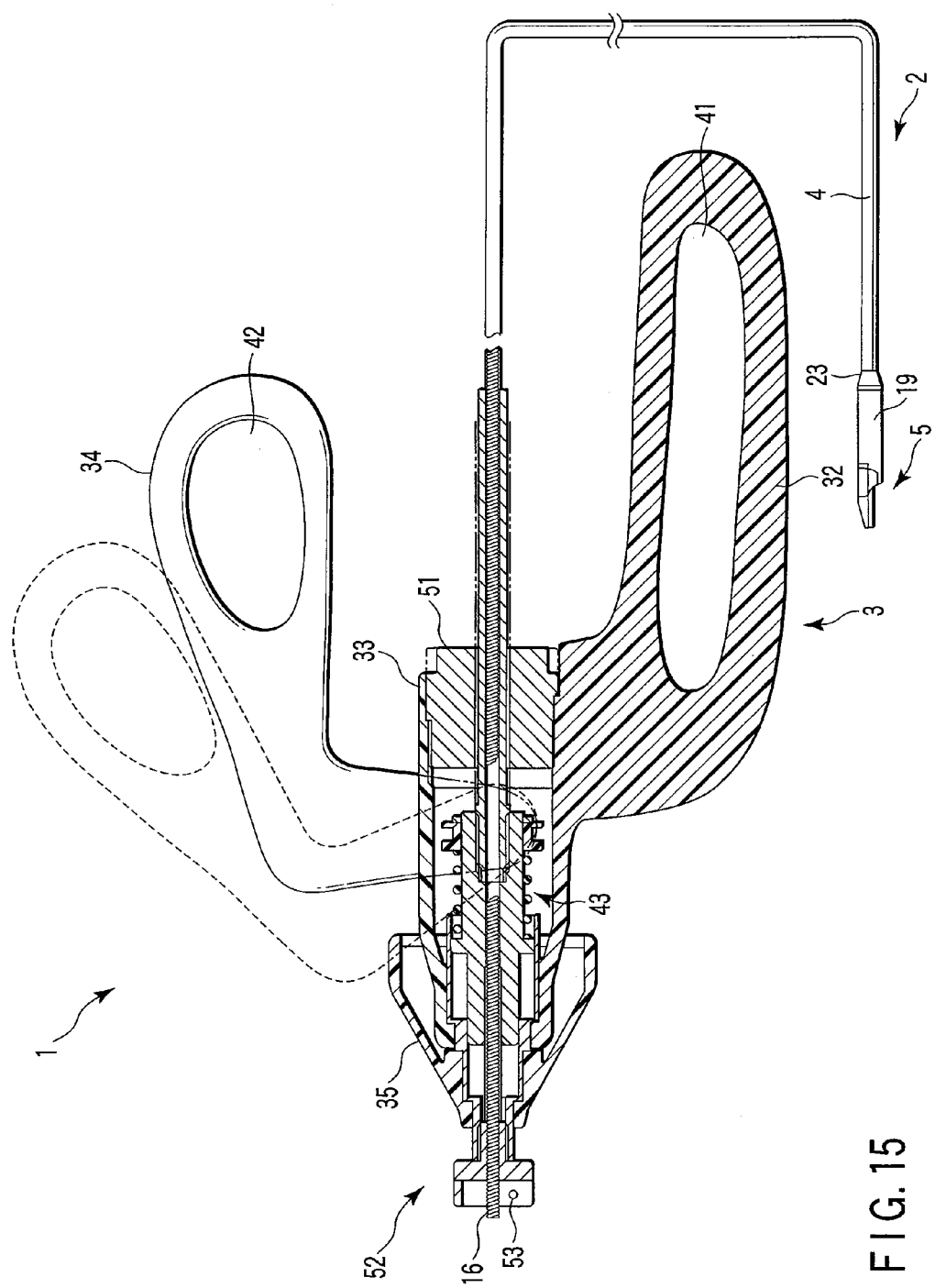
FIG. 15 is an illustrative drawing for explaining an operating state of a movable handle of an operation portion of the ultrasonic clotting and incising apparatus according to the first embodiment.

As shown in FIGS. 11A to 11D, the cover member 19 includes a notched portion 19*b* formed at a distal end of a cylindrical cover member main body 19*a*. The notched portion 19*b* is formed by notching a portion of an outer peripheral surface of the cover member main body 19*a* having a circular sectional configuration, namely, an upper portion of the cover member main body 19*a* in FIGS. 11C and 11D. Further, two vertically long flat surfaces 19*d* formed in parallel flat surfaces are formed on both side portions of a peripheral wall portion with a C-shaped sectional shape positioned below the notched portion 19*b* at a distal end of the cover member main body 19*a*, as shown in FIG. 11D. Elongated holes 19*e* are formed on the two flat surfaces 19*d*, respectively. The elongated holes 19*e* are formed in parallel with a line orthogonal to a direction of the center line of the cover member 19.

The coupling member 21 includes a cylindrical fixing cylindrical body 21*a* and a sliding ring 21*b* fixed to a rear end of the fixing cylindrical body 21*a*. The fixing cylindrical body 21*a* is fixed to a rear end inner peripheral surface of the cover member main body 19*a* by such means as adhesion, welding, or soldering.

The inner ring 22 includes three stage rings different in diameter (a front stage ring 22*a* disposed at a distal end position, a middle stage ring 22*b* disposed at a middle stage position, and a rear stage ring 22*c* disposed at a rear end position). The rear stage ring 22*c* is formed to have approximately the same diameter as an inner diameter of the sheath 4. The rear stage ring 22*c* is fixed to an inner peripheral surface of the sheath 4 in a state that it has been inserted in the sheath 4. The middle stage ring 22*b* is formed to have approximately the same diameter as an inner diameter of the sliding ring 21*b* of the coupling member 21. The front stage ring 22*a* is formed to have a diameter larger than the inner diameter of the sliding ring 21*b* of the coupling member 21.

The rear end of the outer ring 23 is fixed to an outer peripheral surface of the sheath 4 in a state that it has been fitted on the outer peripheral surface of the sheath 4. A distal end of the outer ring 23 is fixed to the middle stage ring 22*b* of the inner ring 22 by such means as screw cramp, adhesion, welding, or soldering. The sliding ring 21*b* of the coupling member 21 is rotatably held between the outer ring 23 and the inner ring 22 in a state that it is sandwiched between the front stage ring 22*a* of the inner ring 22 and the distal end of the outer ring 23.

Figure 3:
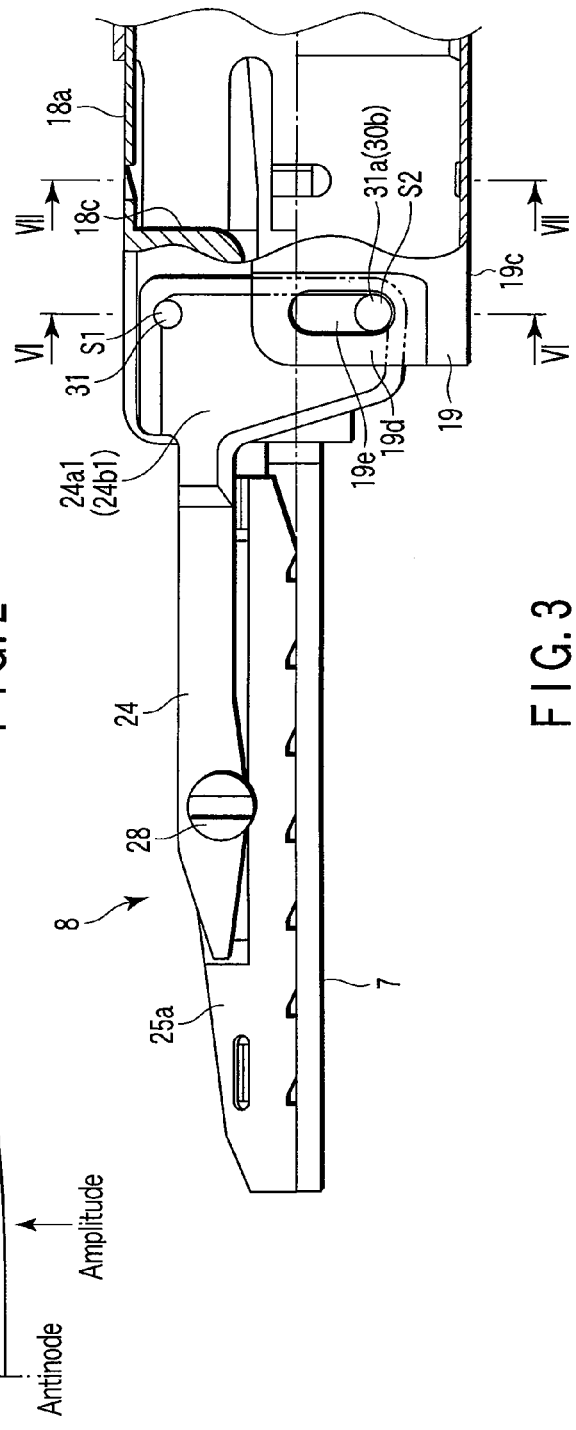
FIG. 3 is a side view showing a distal end of the procedure portion of the ultrasonic clotting and incising apparatus according to the first embodiment in an enlarged manner.

The jaw 8 is caused to face the probe portion 7 and it is driven to be opened and closed to the probe portion 7. As shown in FIG. 3 and FIG. 14, the jaw 8 includes a jaw main body 24 made from metal, a grasping portion holding portion 25*a* made from metal, and a grasping member 25*b* (see FIG. 5) made from resin. The grasping member 25*b* is attached to the grasping portion holding portion 25*a* and it grasps a body tissue between the same and the probe portion 7.

Figure 10A:
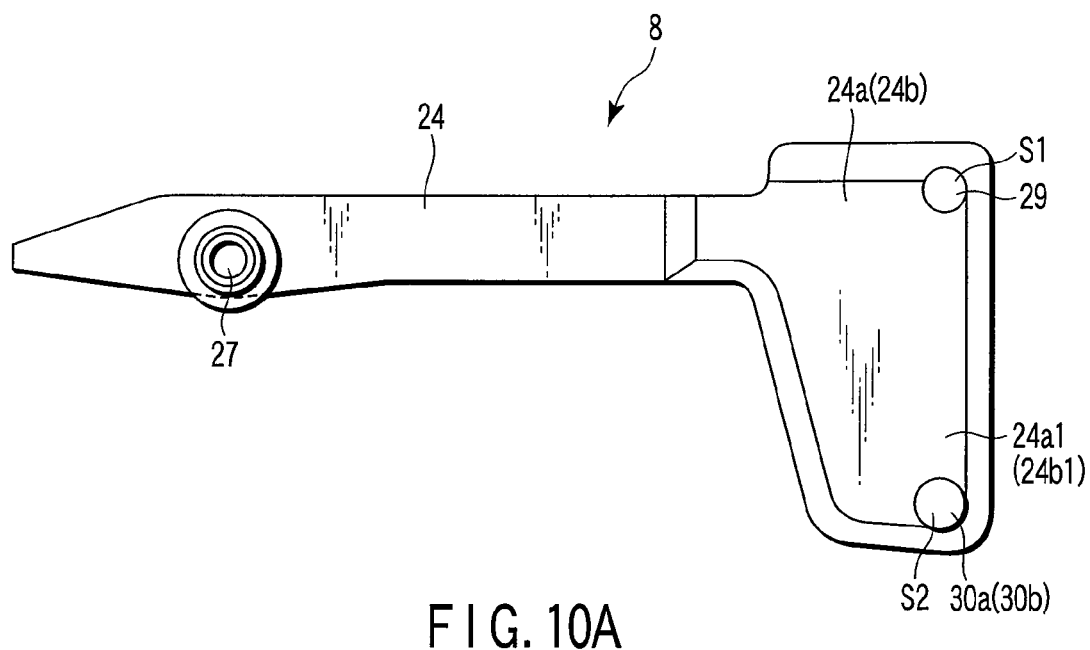
FIG. 10A is a side view showing a jaw of the ultrasonic clotting and incising apparatus according to the first embodiment.
Figure 10B:
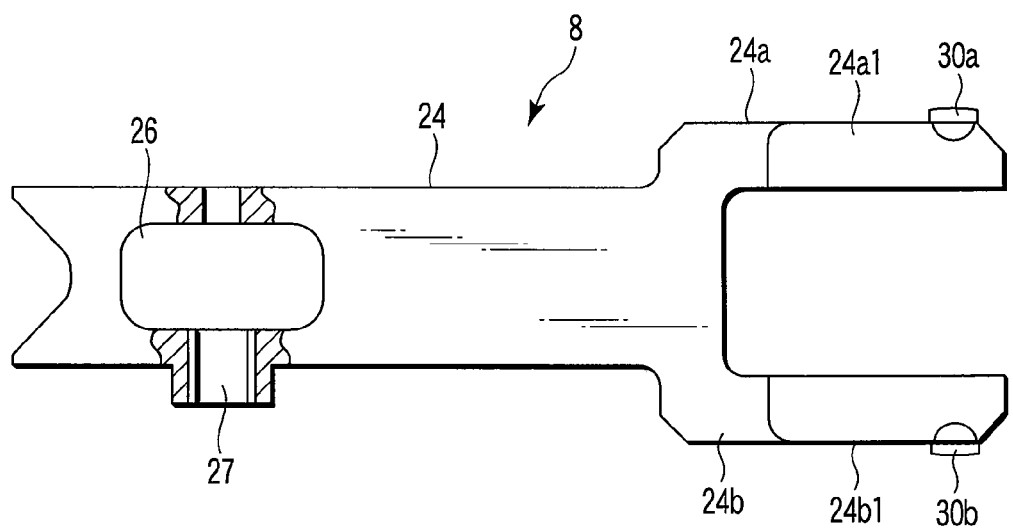
FIG. 10B is a plan view showing the jaw of the ultrasonic clotting and incising apparatus according to the first embodiment.

FIGS. 10A and 10B show the jaw main body 24. As shown in FIG. 10B, a grasping member mounting hole 26 and a screw hole 27 extending through the grasping member mounting hole 26 are formed at the distal end of the jaw main body 24. An engagement projection portion 25*a*1 provided on an upper end of the grasping portion holding portion 25*a* in a projecting manner is inserted into the grasping member mounting hole 26. As shown in FIG. 13, a fixing screw 28 is screwed in the screw hole 27. The grasping portion holding portion 25*a* is supported to the jaw main body 24 so as to be capable of swinging around the fixing screw 28.

As shown in FIG. 10B, two arm portions 24*a* and 24*b* arranged in parallel are provided at a proximal end of the jaw main body 24. As shown in FIG. 10A, projecting portions 24*a*1 and 24*b*1 projecting in a direction perpendicular to a longitudinal direction of the jaw main body 24 are provided on the two arm portions 24*a* and 24*b* in a projecting manner, respectively.

Supporting point pin insertion holes 29 are formed in the arm portions 24*a* and 24*b* of the jaw main body 24 on the upper side in FIG. 10A. Further, an operating pins 30*a* and 30*b* are provided at lower side portions of the two arm portions 24*a* and 24*b*, as shown in FIG. 10A. As shown in FIG. 10B, the operating pins 30*a* and 30*b* are provided on the two arm portions 24*a* and 24*b* so as to project outwardly, respectively.

As shown in FIG. 6, a supporting point pin 31 is rotatably inserted in the supporting point pin insertion holes 29 of the jaw main body 24 and the pin insertion hole 18*d* of the horn cover 18. The jaw main body 24 is rotatably held on the horn cover 18 by the supporting point pin 31. Thereby, a supporting point S1 supporting the jaw main body 24 in a state that the jaw main body 24 does not move relative to the probe portion 7 axially thereto by the supporting point pin 31 is formed.

The operating pins 30*a* and 30*b* of the jaw main body 24 are inserted and maintained in the elongated holes 19*e* of the cover member 19. The cover member 19 is supported so as to be movable relative to the casing 10 of the ultrasonic transducer unit 6 axially relative to the probe portion 7. The jaw 8 is operated to an opened position shown in FIG. 14 and a closed position shown in FIG. 3 for opening and closing according to movement of the cover member 19 at this time. Thereby, an operating point S2 movable axially relative to the probe portion 7 together with the cover member 19 at an operating time at which the cover member 19 moves axially relative to the probe portion 7 is formed by two operating pins 30*a* and 30*b*.

The operating portion 3 mainly includes a fixed handle 32, a holding cylinder 33, a movable handle 34, and a rotatable knob 35. The holding cylinder 33 is disposed on an upper portion of the fixed handle 32. The movable handle 34 operates the jaw 8 for opening and closing. The rotatable knob 35 rotationally drives the probe portion 7 and the jaw 8 configuring a distal end procedure portion of the distal end unit 5 circumferentially relative to the probe portion 7.

The movable handle 34 includes an approximately U-shaped arm portion 36. As shown in FIG. 17, the U-shaped arm portion 36 includes two arms 36*a* and 36*b*. The movable handle 34 is assembled to the holding cylinder 33 in a state that the holding cylinder 33 is inserted between the two arms 36*a* and 36*b*.

The arms 36*a* and 36*b* include supporting pins (supporting member) 37 and an operating pins (actuating portion) 38, respectively. Pin receiving holes 39 and window portions 40 are formed in both sides of the holding cylinder 33, respectively. The supporting pin 37 of each of the arms 36*a* and 36*b* is inserted into the pin receiving hole 39. Thereby, an end of the movable handle 34 is rotatably pivoted to the holding cylinder 33 via the supporting pins 37.

The fixed handle 32 and the movable handle 34 are provided with finger ring portions 41 and 42, respectively. The movable handle 34 is rotated via the supporting pins 37 by inserts operator's fingers in the finger ring portions 41 and 42 to grasp the fixed handle 32 and the movable handle 34, so that the movable handle 34 is operated to be opened and closed to the fixed handle 32.

The respective operating pins 38 of the movable handle 34 extend in the holding cylinder 33 through the window portions 40 of the holding cylinder 33. An operation force transmitting mechanism 43 transmitting operation force of the movable handle 34 to the sheath 4 which is a driving member of the jaw 8 is provided in the holding cylinder 33.

Figure 16:
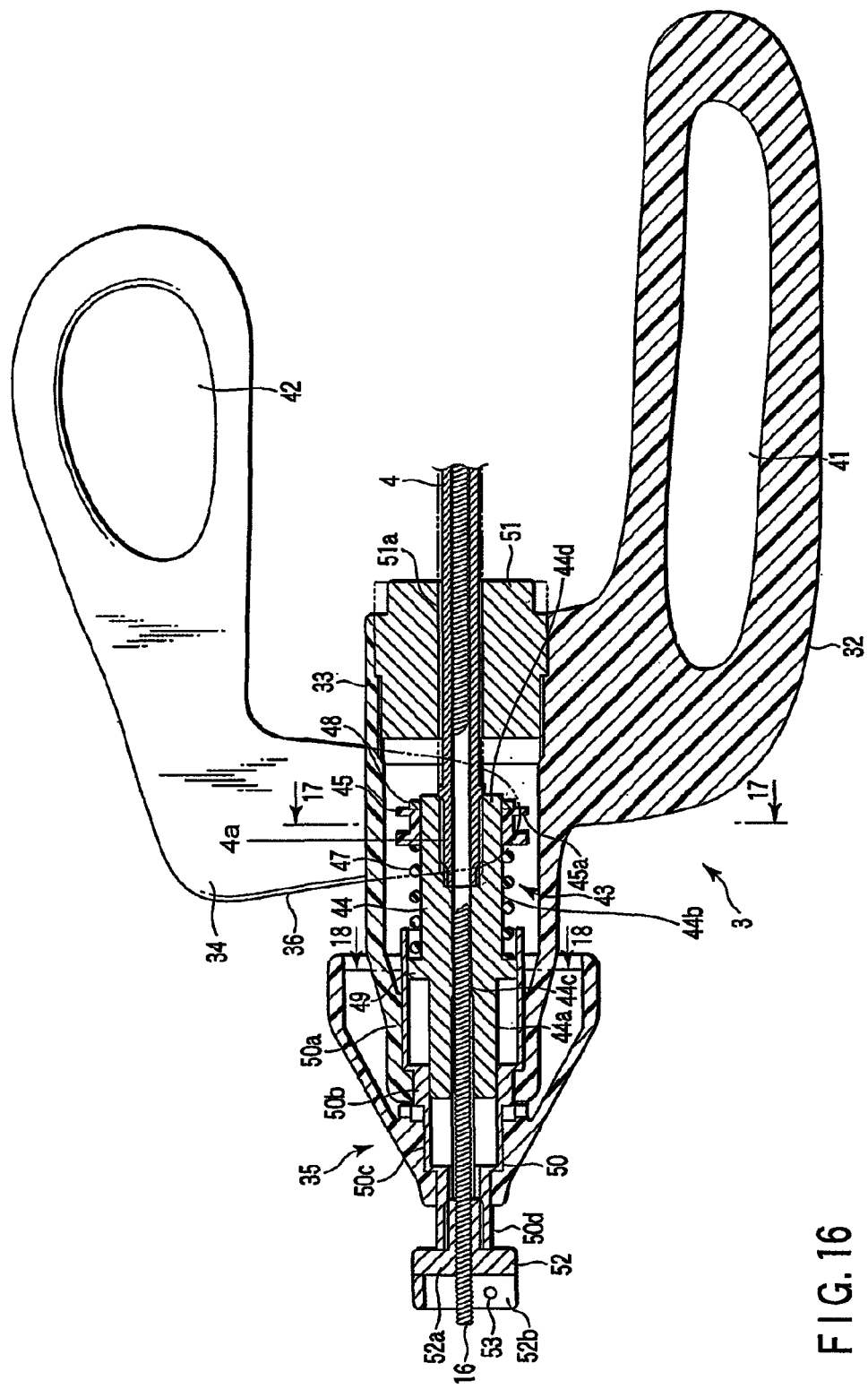
FIG. 16 is a vertical sectional view showing an internal configuration of the operation portion of the ultrasonic clotting and incising apparatus according to the first embodiment.

FIG. 16 shows an internal structure of the operation portion 3. As shown in FIG. 16, the operation force transmitting mechanism 43 mainly includes an approximately cylindrical spring catching member 44 made from metal and a slider member 45 made from resin. The spring catching member 44 is disposed coaxially with the center line of the holding cylinder 33.

An intermediate coupling cylindrical body 50 is disposed in the holding cylinder 33. The intermediate coupling cylindrical body 50 includes four stage cylindrical portions 50*a*, 50*b*, 50*c*, and 50*d* different in outer diameter. Setting is performed such that the first cylindrical portion 50*a* positioned at the most leading position has the largest diameter, the second cylindrical portion 50*b* positioned at the second stage has the second-largest diameter, the third cylindrical portion 50*c* positioned at the third stage has the third-large diameter, and the fourth cylindrical portion 50*d* positioned at the fourth stage has the smallest diameter.

A proximal end of the holding cylinder 33 is fixed to a proximal end outer peripheral surface of the first cylindrical portion 50*a* and an outer peripheral surface of the second cylindrical portion 50*b* of the intermediate coupling cylindrical body 50 such that the former is fitted on the latter. A proximal end of the rotatable knob 35 is fixed to a proximal end outer peripheral surface of the third cylindrical portion 50*c* and an outer peripheral surface of the fourth cylindrical portion 50*d* of the intermediate coupling cylindrical body 50 in a state that the former is fitted on the latter.

A proximal end side engagement portion 44*a* inserted in the third cylindrical portion 50*c* of the intermediate coupling cylindrical body 50 is formed on an outer peripheral surface of the spring catching member 44 on its proximal end side. Further, a slider guide portion 44*b* having a diameter smaller than an inner diameter of the first cylindrical portion 50*a* of the intermediate coupling cylindrical body 50 is formed on an outer peripheral surface of the spring catching member 44 on its distal end side thereof. A spring catching potion 49 having the largest diameter is provided between the proximal end side engagement portion 44*a* and the slider guide portion 44*b* in a projecting manner. The spring catching potion 49 is formed to have a diameter approximately equal to the inner diameter of the first cylindrical portion 50*a* of the intermediate coupling cylindrical body 50. A proximal end of the spring catching member 44 is coupled to a proximal end of the holding cylinder 33 so as to be capable of rotating circumferentially via the intermediate coupling cylindrical body 50 and be capable of advancing and retreating in the same direction as the center line of the holding cylinder 33.

An insertion hole 44*c* in which the coil shaft 16 is inserted to be movable axially is formed at an axial center portion of the spring catching member 44. A screw hole 44*d* having a diameter larger than the diameter of the insertion hole 44*c* is formed at a distal end of the insertion hole 44*c*. A proximal end 4*a* of the sheath 4 is threadably fixed in the screw hole 44*d*.

A coil spring 47, the slider member 45, and a stopper 48 are disposed on an outer peripheral surface of the spring catching member 44. A rear end of the coil spring 47 is fixed to the spring catching potion 49. The stopper 48 restricts a movement position of the slider member 45 on a front end side thereof. The coil spring 47 is confined between the spring catching potion 49 and the slider member 45 with a fixed confinement force.

A ring-shaped engagement groove 45*a* is formed on an outer peripheral surface of the slider member 45 so as to extend circumferentially thereto. The operating pins 38 of the movable handle 34 are engaged with the engagement groove 45*a* in a state that they have been inserted in the engagement groove 45*a*, as shown in FIG. 17. Incidentally, the jaw main body 24 of the jaw 8 is normally held in an opened position where it is separated from the probe portion 7, as shown in FIG. 14.

When an operator grasps the movable handle 34 to operate the movable handle 34 so as to be closed to the fixed handle 32, the operating pins 38 are rotated about the supporting point pins 37 according to a rotating action of the movable handle 34 at this time. The slider member 45 is moved in a retreating direction axially in association with the action of the operating pins 38. At this time, the spring catching member 44 coupled to the slider member 45 via the coil spring 47 is also moved in a retreating direction axially together with the slider member 45. Thereby, operation force of the movable handle 34 is transmitted to the slider member 45 and the spring catching member 44 via the pair of operating pins 38. Therefore, the sheath 4 serving as a driving member for the jaw 8 is moved in a retreating direction. As a result, the jaw main body 24 of the jaw 8 is rotated via the supporting point pin 31 so that the jaw main body 24 of the jaw 8 is operated to move to a closed position while approaching the probe portion 7, as shown in FIG. 3.

Further, when a body tissue is clamped between the grasping member 25*b* of the jaw 8 and the probe portion 7 according to this operation, the grasping member 25*b* is rotated about the fixing screw 28 by a fixed angle according to flexure of the probe portion 7 so that force acts over the entire length of the grasping member 25*b* evenly. By outputting ultrasonic waves in this state, clotting or incising of a body tissue such as a blood vessel is made possible.

A closing member 51 is fixed at a front end of the holding cylinder 33. An insertion hole 51*a* in which the sheath 4 is inserted to be movable axially is formed at an axial center portion of the closing member 51.

A coil shaft fixing member 52 is fixed at a rear end of the intermediate coupling cylindrical body 50. An insertion hole 52*a* in which the coil shaft 16 is inserted is formed at an axial center portion of the coil shaft fixing member 52. As shown in FIG. 19, a slit 52*b* extending from an outer peripheral surface of a peripheral wall portion of the coils shaft fixing member 52 inwardly is formed on the peripheral wall portion. The slit 52*b* is formed so as to extend through the insertion hole 52*a*. A fixing screw 53 is screwed between wall surfaces of both sides of the slit 52*b*. Elastic deformation is caused to a state where a width between the wall surfaces of both sides of the slit 52*b* becomes narrow according to tightening of the fixing screw 53. Thereby, the coil shaft 16 inserted in the axial center portion of the coil shaft fixing member 52 is tightened and fixed to the coil shaft fixing member 52. As a result, the coil shaft 16 is integrally fixed to the rotatable knob 35 via the coil shaft fixing member 52 and the intermediate coupling cylindrical body 50. Therefore, rotational operating force of the rotatable knob 35 is transmitted to the coil shaft 16 via the intermediate coupling cylindrical body 50 and the coil shaft fixing member 52 at a rotational operating time of the rotatable knob 35 so that the coil shaft 16 is rotated circumferentially. Further, rotation of the coil shaft 16 is transmitted to the casing 10 of the ultrasonic transducer 9 via the end plate 12 so that the probe portion 7 and the jaw 8 serving as the distal end procedure portion of the distal end unit 5 are rotationally driven circumferentially relative to the probe portion 7. At this time, rotational operating force of the rotatable knob 35 is not transmitted to the spring catching member 44. Therefore, the sheath 4 is held in a state that it is not linked to rotation of the rotatable knob 35.

In the first embodiment, as shown in FIG. 3, the jaw 8 is set to a state that the operating point S2 and the supporting point S1 are positioned on a line orthogonal to the center line of the probe portion 7 in a state that the jaw 8 has been closed to the probe portion 7.

In the ultrasonic clotting and incising apparatus 1 according to the first embodiment, a length of the sheath 4 is set to a length suitable for use in a combination with a hard endoscope such as, for example, a large intestine mirror inserted in a rectum. For example, setting is performed such that a length of the sheath 4 is in a range from about 200 to 400 mm, a length of the distal end unit 5 is about 90 mm, and an outer diameter φ of the distal end unit 5 is about 8.6 mm, respectively. Further, the ultrasonic transducer 9 is set such that a resonant frequency is 47 kHz and an amplitude is 60 µmp-p, respectively. An entire length of the ultrasonic transducer 9 is a half wavelength and a distal end of the probe portion 7 and a rear end the ultrasonic transducer 9 are set at antinodes of vibration, as shown in FIG. 2. A node portion of vibration near an intermediate of the ultrasonic transducer 9 is at a position where the amplitude is zero and where the ultrasonic transducer 9 is engaged with the casing 10.

Next, an operation of the embodiment will be explained. The ultrasonic clotting and incising apparatus 1 according to the embodiment is used in combination with a hard endoscope such as, for example, a large intestine mirror inserted in a rectum at a use time thereof. The distal end of the insertion portion 2 is inserted up to a position near a target body tissue to be treated. Subsequently, the position of the jaw 8 and the probe portion 7 is adjusted to a rotating position where the target body tissue can be grasped easily by rotationally operating the rotatable knob 35. At this time, the coil shaft 16 is rotationally driven by rotational operating force of the rotatable knob 35 so that the probe portion 7 and the jaw 8 configuring the distal end procedure portion of the distal end unit 5 are rotationally driven circumferentially relative to the probe portion 7 according to the rotation of the coil shaft 16. Incidentally, the rotational operating force of the rotatable knob 35 is not transmitted to the spring catching member 44. Therefore, the sheath 4 is held in a state that it is not linked to the rotation of the rotatable knob 35.

After adjusting the position of the jaw 8 and the probe portion 7, an operator grasps the movable handle 34 to operate the movable handle 34 to be closed to the fixed handle 32. As described above, the sheath 4 which is the driving member for the jaw 8 is moved in a retreating direction according to the closing operation of the movable handle 34. As a result, the jaw main body 24 of the jaw 8 is rotated via the supporting point pin 31 so that the jaw main body 24 of the jaw 8 is operated to move to a closed position while approaching the probe portion 7, as shown in FIG. 3.

Further, when a body tissue is clamped between the grasping member 25b of the jaw 8 and the probe portion 7 according to this operation, the grasping member 25b is rotated about the fixing screw 28 by a fixed angle according to flexure of the probe portion 7 so that force acts over the entire length of the grasping member 25b evenly. By outputting ultrasonic waves in this state, clotting or incising of a body tissue such as a blood vessel is made possible.

Effects of the first embodiment are described below. That is, in the ultrasonic clotting and incising apparatus 1 according to the embodiment, as shown in FIG. 3, the jaw 8 is set such that the operating point S2 and the supporting point S1 are positioned on a line orthogonal to the center line of the probe portion 7 in a state that the jaw 8 has been closed to the probe portion 7. Therefore, when an operator grasps the movable handle 34 to operate the movable handle 34 so as to be closed to the fixed handle 32, transmission efficiency of force grasping a body tissue between the grasping member 25b of the jaw 8 and the probe portion 7 in a final stage can be improved. Thereby, loss of an amount of grasping force of the jaw 8 to force for pulling the sheath 4 when the operator operates the movable handle 34 for closing (a force amount for closing the jaw 8) is reduced so that a high amount of grasping force can be obtained. As a result, even when the ultrasonic clotting and incising apparatus 1 according to the embodiment is used in combination with a flexible endoscope, operating force exerted when the operator operates the movable handle 34 for closing can be transmitted to the jaw 8 of the procedure portion accurately so that action for closing the jaw 8 can be performed stably.

Further, since the sheath 4 is formed of a flexible pipe where a blade which is a mesh pipe made of metal wire is accommodated in a resin tube, stretch of the sheath 4 axially when pulling force axially relative to the sheath 4 is caused to act on the sheath 4 can be reduced. Thereby, the operator can perform an operation for closing the jaw 8 accurately when the operator operates the movable handle 34 for closing. Therefore, by assembling a small-sized ultrasonic transducer 9 in the distal end unit 5 disposed at the distal end of the sheath 4, high resection ability can be obtained even when a vibration velocity of ultrasonic vibration is low. That is, in the small-sized ultrasonic transducer 9, the vibration velocity is low, but compensation for lowering of the vibration velocity can be performed by increasing an amount of grasping force exerted when the operator closes the jaw 8. Incidentally, the resection ability is proportional to vibration velocity×amount of grasping force. By transmitting operation force exerted when the operator operates the movable handle 34 for closing to the jaw 8 without generating loss as much as possible, an amount of grasping force exerted when the operator closes the jaw 8 can be increased.

The cover member 19 is coupled to the distal end of the sheath 4 in a state that it can be rotated circumferentially relative to the probe portion 7 and axial movement of the probe portion 7 follows the sheath 4. Thereby, even when the probe portion 7 and the jaw 8 of the distal end unit 5 are rotationally driven circumferentially relative to the probe portion 7 at a rotational operating time of the rotatable knob 35, the sheath 4 is held in a state that it is not linked to rotation of the rotatable knob 35.

Further, the operation portion 3 includes the slider 45 movable axially relative to the sheath 4, the spring catching member 44 guiding movement of the slider 45, the supporting point pins 37 rotatably supporting the movable handle 34, and the operating pins 38 moving the slider 45 axially relative to the sheath 4 in association with action where the movable handle 34 rotates about the supporting point pins 37. The proximal end 4a of the sheath 4 includes the fixation portion fixed to the screw hole 44d of the slider 45. Thereby, the sheath 4 moves axially relative to the sheath 4 in association with opening and closing operations of the movable handle 34. At this time, rotational operating force of the rotatable knob 35 is not transmitted to the spring catching member 44. Therefore, the sheath 4 is held in a state that it is not linked to rotation of the rotatable knob 35.

Further, the operation portion 3 includes the rotatable knob 35 rotating circumferentially relative to the sheath 4. The coil shaft 16 is inserted in the sheath 4 to be rotatable circumferentially. The proximal end of the coil shaft 16 is connected to the rotatable knob 35 and the distal end thereof is fixed to the casing 10. Thereby, rotational operating force of the rotatable knob 35 is transmitted to the casing 10 via the coil shaft 16 with excellent rotational follow-up so that the probe portion 7 and the jaw 8 of the distal end unit 5 can be rotationally driven circumferentially relative to the probe portion 7. Therefore, an operator can change a direction of the jaw 8 arbitrarily by rotational operation of the rotatable knob 35. At this time, the sheath 4 is not linked to the rotatable knob 35 and it can transmit only an opening or closing action to operate the movable handle 34 to the jaw 8. Accordingly, an ultrasonic operating apparatus which can be used in combination with a flexible endoscope, for example, and can clot and incise a body tissue even at a low vibration velocity can be provided.

FIG. 20 to FIG. 26 show a second embodiment of the present invention. The present embodiment has such a configuration that the configuration of the distal end unit 5 of the ultrasonic clotting and incising apparatus 1 according to the first embodiment (see FIG. 1 to FIG. 19) has been modified as described below. The other configuration of the second embodiment is similar to that of the first embodiment.

That is, in the second embodiment, a length of the sheath 4 is set to a length suitable for use in combination with, for example, a flexible endoscope (not shown) or an over tube (not shown) attached to a flexible endoscope. For example, setting is performed such that a length of the sheath 4 is about 1.5 mm, a length of the distal end unit 5 is about 30 mm, and an outer diameter φ of the distal end unit 5 is about 5.9 mm, respectively. Further, the ultrasonic transducer 9 is set such that a resonant frequency is 100 kHz and an amplitude is 20 ump-p, respectively. An entire length of the ultrasonic transducer 9 is a half wavelength, and a distal end of the probe portion 7 and a rear end the ultrasonic transducer 9 are set at antinodes of vibration, as shown in FIG. 2. A node portion of vibration near an intermediate of the ultrasonic transducer 9 is at a position where the amplitude is zero and where the ultrasonic transducer 9 is engaged with the casing 10.

Next, an operation of the embodiment will be explained. For example, the insertion portion 2 is inserted in a channel of a flexible endoscope (not shown) or a channel of an over tube (not shown) attached to a flexible endoscope at a use time of the ultrasonic clotting and incising apparatus 1 according to the embodiment. Thus, the ultrasonic clotting and incising apparatus according to the embodiment is used in combination with a flexible endoscope.

Thereafter, operation similar to that of the first embodiment is performed, so that treatment such as clotting or incising of such a body tissue as a blood vessel is performed using the ultrasonic clotting and incising apparatus 1 according to the embodiment in combination with a flexible endoscope.

Accordingly, since a length of the distal end unit 5 of the second embodiment is shorter than that of the first embodiment, flexibility of the insertion portion 2 inserted in the channel of the flexible endoscope can be further increased. As a result, for example, work using the ultrasonic clotting and incising apparatus 1 according to the embodiment in combination with a flexible endoscope can be made further easy.

Further, as shown in FIG. 20, in the jaw 8 according to the embodiment, a pin insertion hole 61 extending in a direction perpendicular to the axis of the probe portion 7 is formed in the grasping portion holding portion 25a of the jaw main body 24 made from metal. A fixing pin 62a of a grasping member 62 made from resin is fixed to the pin insertion hole 61 in a state that it has been inserted therein. Therefore, a configuration of the jaw 8 can be made simpler than that of the first embodiment and an entire size of the jaw 8 can be reduced as compared with that of the first embodiment.

Figure 27:
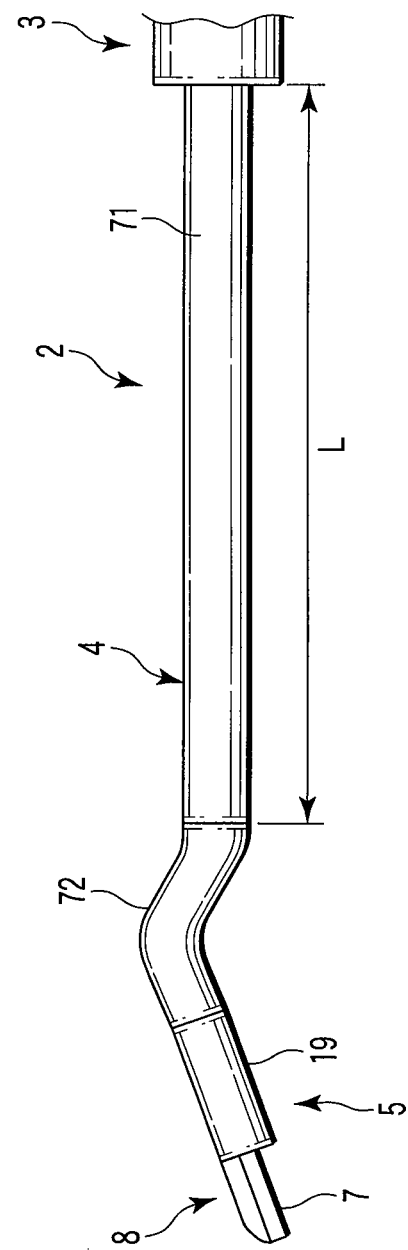
FIG. 27 is a side view showing a modified embodiment of the insertion portion of the ultrasonic clotting and incising apparatus according to the first embodiment.

FIG. 27 shows a modified embodiment of the insertion portion 2 of the ultrasonic clotting and incising apparatus 1 according to the first embodiment (see FIGS. 1 to 19). The sheath 4 of the insertion portion 2 of the modified embodiment includes a hard pipe body 71 formed of a hard pipe body and having a distal end and a proximal end, such as, for example, a metal pipe, and a bendable and deformable bending portion 72 coupled to a distal end of the hard pipe body 71. The bending portion 72 can be operated in a bending manner according to operation of a bending operation knob (not shown) attached to the operation portion 3 or the like in the same manner as the bending portion of the endoscope.

Setting is performed such that the length of the hard pipe body 71 is in a range from about 200 to 400 mm, the length of the bending portion 72 is in a range from about 10 to 50 mm, and the length of the distal end unit 5 is equal to that of the first embodiment.

Therefore, it is preferable that the ultrasonic clotting and incising apparatus 1 having the sheath 4 of the insertion portion 2 of the modified embodiment is used in combination with a hard endoscope such as, for example, a large intestine mirror inserted in a rectum. Work using the ultrasonic clotting and incising apparatus 1 according to the modified embodiment in combination with an endoscope can be made further easy.

Incidentally, the present invention is not limited to the abovementioned embodiments, but it can be implemented without departing from the spirit or scope of the present invention while modified variously.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical instrument comprising:
   a tubular casing configured to define a center line extending in a forward-backward direction;
   a cover member disposed on an outer side of the casing and configured to move the forward-backward direction relative to the casing;
   a jaw having a distal end, a proximal end, and two arms provided on the proximal end and spaced apart from each other;
   a supporting portion disposed between the two arms and the casing, and being configured such that the casing pivotally supports the two arms with the supporting portion; and
   two action portions disposed respectively between the two arms and the cover member, where the cover member connects with the two arms through the two action portions such that the two arms rotate with respect to the cover member in response to movements of the cover member;

wherein:
the supporting portion and the two action portions are orthogonal or substantially orthogonal relative to the center line,
the center line exists between the supporting portion and the two action portions, and
the distal end of the jaw is moved closer to the center line when the cover member is moved to the backward direction relative to the casing, and
is moved farther to the center line when the cover member is moved to the forward direction relative to the casing.

2. The surgical instrument according to claim 1, wherein:
the cover member further includes:
a tubular cover member main body having a distal portion disposed on the action portions, and
a notched portion formed on the distal end of the cover member main body and configured to expose the casing disposed on the supporting portion relative to the cover member main body.

3. The surgical instrument according to claim 2, wherein the cover member includes two flat surfaces formed as a parallel flat surface on both side portions which is provided on the distal portion of the cover member main body and disposed on the action portions.

4. The surgical instrument according to claim 3, wherein the two arms are disposed on an inner side of the two flat surfaces.

5. The surgical instrument according to claim 2, wherein the cover member includes two elongated holes at its inner side for moving the action portions, the elongated holes being provided at the distal end of the cover member main body and including a longitudinal direction at a direction parallel to a line orthogonal or substantially orthogonal to the center line.

6. The surgical instrument according to claim 1, wherein the jaw includes:
a jaw main body including the two arms;
a jaw member disposed at a distal end of the jaw main body; and
a rotation axis disposed between the distal end of the jaw main body and the jaw member and configured to be capable of swinging around the jaw member with respect to the jaw main body.

7. The surgical instrument according to claim 1, comprising:
an ultrasonic transducer configured to be accommodated into the casing and to generate ultrasonic vibration; and
a probe facing the jaw and configured to transmit the ultrasonic vibration from the ultrasonic transducer.

8. The surgical instrument according to claim 1, further comprising:
a sheath including a distal end coupled to the cover member and a proximal end and the sheath configured to be flexible; and
an operation portion disposed on the proximal end of the sheath and configured to operate the cover member relative to the casing.

9. The surgical instrument according to claim 8, wherein the cover member and the sheath are configured to move axially relative to the center line.

10. The surgical instrument according to claim 8, wherein the sheath includes a resin tube and a mesh-like blade formed of a metal wire configured to be received in the resin tube.

11. The surgical instrument according to claim 8, wherein the operation portion includes:
a holding member;
a slider axially movable relative to the sheath;
a guide member configured to guide the slider;
a supporting member disposed on the holding member and configured to rotatably support a movable handle; and
an actuating portion configured to move the slider axially relative to the sheath, in association with rotating action of the movable handle about the supporting member, and
the sheath includes a fixation portion fixed to the slider at the proximal end thereof, the fixation portion configured to move axially relative to the sheath, in conjunction with opening and closing actions of the movable handle.

12. The surgical instrument according to claim 11, wherein the operation portion includes a rotatable knob configured to rotate circumferentially relative to the sheath,
the sheath includes a coil shaft therein, having a distal end and a proximal end,
the proximal end of the coil shaft is connected to the rotatable knob, and
the distal end of the coil shaft is fixed to the casing.

13. The surgical instrument according to claim 12, wherein the coil shaft is configured to be rotationally driven by rotational operating force of the rotatable knob so that the casing is rotationally driven circumferentially relative to the center line in accordance with rotation of the coil shaft.

14. The surgical instrument according to claim 8, wherein the sheath includes a hard pipe body formed of a hard tubular body and having a distal end and a proximal end, and a bending portion coupled to the distal end of the hard pipe body and deformable in a bending manner.

* * * * *